United States Patent [19]

Onopchenko et al.

[11] 4,102,932
[45] * Jul. 25, 1978

[54] BETA, BETA-DIALKYLETHYLMERCAPTOE-THOXYLATES AS NEW COMPOUNDS

[75] Inventors: Anatoli Onopchenko, Monroeville; Johann G. Schulz, Pittsburgh, both of Pa.

[73] Assignee: Gulf Research & Development Company, Pittsburgh, Pa.

[*] Notice: The portion of the term of this patent subsequent to Feb. 22, 1994, has been disclaimed.

[21] Appl. No.: 759,420

[22] Filed: Jan. 14, 1977

Related U.S. Application Data

[63] Continuation-in-part of Ser. No. 600,150, Jul. 29, 1975, Pat. No. 4,009,211.

[51] Int. Cl.$^2$ .................................... C07C 149/18
[52] U.S. Cl. ............................ 260/609 R; 252/135
[58] Field of Search ................................ 260/609 R

[56] References Cited

U.S. PATENT DOCUMENTS

| | | | |
|---|---|---|---|
| 2,494,610 | 1/1950 | Davidson et al. | 260/609 R |
| 2,619,466 | 11/1952 | Wolf | 252/89 |
| 2,905,720 | 9/1959 | de Benneville et al. | 260/609 R |
| 3,174,900 | 3/1965 | Wyant | 260/609 R |

Primary Examiner—Lewis Gotts
Assistant Examiner—Molly C. Eakin

[57] ABSTRACT

Beta,beta-dialkylethylmercaptoethoxylates as new compounds.

13 Claims, No Drawings

BETA, BETA-DIALKYLETHYLMERCAPTOETHOXYLATES AS NEW COMPOUNDS

This application is a continuation-in-part application of our application Ser. No. 600,150, now U.S. Pat. No. 4,009,211 entitled Beta,Beta-Dialkylethylmercaptoethoxylates as New Compounds, filed July 29, 1975.

BACKGROUND OF THE INVENTION

1. Field of the Invention

This invention relates to beta,beta-dialkylethylmercaptoethoxylates as new compounds that possess improved detergency properties.

2. Description of the Prior Art

Many effective detergents have been prepared using normal alpha olefins as a component thereof. In the preparation of normal alpha olefin using the Ziegler process wherein ethylene is oligomerized in the presence of an aluminum alkyl, vinylidene olefins are also obtained as a by-product. The composition defined and claimed herein can utilize such vinylidene olefin as a component thereof.

SUMMARY OF THE INVENTION

In our application Ser. No. 600,150, referred to above, we have claimed the following beta,beta-dialkylethylmercaptoethoxylate as a new compound possessing improved detergency properties:

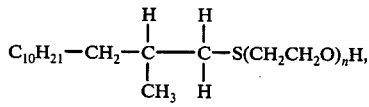

wherein $n$ is an integer from 8 to 16. We are herein claiming the following beta,beta-dialkylethylmercaptoethoxylates as new compounds possessing unique detergency properties, particularly in washing polyester fabrics:

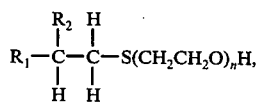

wherein $R_1$ and $R_2$, the same or different, are alkyl substituents having from one to ten carbon atoms, with the number of carbon atoms in $R_1 + R_2$ totaling 10, 14 or 16, and

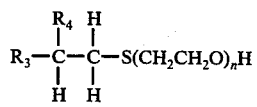

wherein $R_3$ and $R_4$, the same or different, are alkyl substituents having from two to ten carbon atoms, with the number of carbon atoms in $R_3 + R_4$ totaling 12, and $n$ is an integer greater than 3, preferably from 8 to 26, but most preferably from 8 to 16, sufficient to give substantially complete miscibility in water. Specific examples of alkyl substituents that can be present in the above formulas are ethyl, propyl, n-butyl, n-pentyl, isopropyl, isobutyl, 4-methylhexyl, 5-ethyloctyl, 3,6-dimethyloctyl, etc.

Among the specific compounds that are included in the above structural formulas are:
2-methylundecylmercaptotriethoxy ethoxylate
2-ethyldecylmercaptotriethoxy ethoxylate
2-n-propylnonylmercaptotriethoxy ethoxylate
2-n-butyloctylmercaptotriethoxy ethoxylate
2-n-pentylheptylmercaptotriethoxy ethoxylate
2-n-hexylhexyltriethoxy ethoxylate
2-ethyldodecylmercaptotriethoxy ethoxylate
2-n-propylundecylmercaptotriethoxy ethoxylate
2-n-butyldecylmercaptotriethoxy ethoxylate
2-n-pentylnonylmercaptotriethoxy ethoxylate
2-n-hexyloctylmercaptotriethoxy ethoxylate
2-n-heptylheptylmercaptotriethoxy ethoxylate
2-methylpentadecylmercaptotriethoxy ethoxylate
2-ethyltetradecylmercaptotriethoxy ethoxylate
2-n-propyltridecylmercaptotriethoxy ethoxylate
2-n-butyldodecylmercaptotriethoxy ethoxylate
2-n-pentylundecylmercaptotriethoxy ethoxylate
2-n-hexyldecylmercaptotriethoxy ethoxylate
2-n-heptylnonylmercaptotriethoxy ethoxylate
2-n-octyloctylmercaptotriethoxy ethoxylate
2-methylheptadecylmercaptotriethoxy ethoxylate
2-n-propylpentadecylmercaptotriethoxy ethoxylate
2-n-butyltetradecylmercaptotriethoxy ethoxylate
2-n-pentyltridecylmercaptotriethoxy ethoxylate
2-n-hexyldodecylmercaptotriethoxy ethoxylate
2-n-heptylundecylmercaptotriethoxy ethoxylate
2-n-octyldecylmercaptotriethoxy ethoxylate
2-n-nonylnonylmercaptotriethoxy ethoxylate, and etc., and the corresponding tetraethoxy, pentaethoxy, hexaethoxy, heptaethoxy, octaethoxy, nonaethoxy, decaethoxy, undecaethoxy, dodecaethoxy, tridecaethoxy, tetradecaethoxy, pentadecaethoxy, hexadecaethoxy and heptadecaethoxy ethoxylates, and the various mixtures of the above.

The novel compounds defined and claimed herein can be prepared by reacting a specific vinylidene olefin, defined hereinafter, with mercaptoethanol to form the corresponding thioether-ethanol adduct and then reacting the adduct so formed with ethylene oxide to obtain the beta,beta-dialkylethylmercaptoethoxylate.

In the reaction between the vinylidene olefin and the mercaptoethanol, the vinylidene olefin that is used can be defined by reference to the following structural formula:

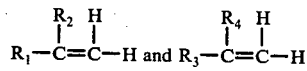

wherein $R_1$, $R_2$, $R_3$ and $R_4$, the same or different, are alkyl substituents as defined above, with the number of carbon atoms in $R_1 + R_2$ and in $R_3 + R_4$ also as defined above. Specific examples of vinylidene olefins that can be used include:
2-methyl-1-undecene
2-ethyl-1-decene
2-n-propyl-1-nonene
2-n-butyl-1-octene
2-n-pentyl-1-heptene
2-n-hexyl-1-hexene
2-ethyl-1-dodecene
2-n-propyl-1-undecene
2-n-butyl-1-decene
2-n-pentyl-1-nonene 2-n-hexyl-1-octene
2-n-heptyl-1-heptene
2-methyl-1-pentadecene
2-ethyl-1-tetradecene
2-n-propyl-1-tridecene
2-n-butyl-1-dodecene
2-n-pentyl-1-undecene
2-n-hexyl-1-decene
2-n-heptyl-1-nonene
2-n-octyl-1-octene
2-methyl-1-heptadecene
2-ethyl-1-hexadecene
2-n-propyl-1-pentadecene
2-n-butyl-1-tetradecene
2-n-pentyl-1-tridecene
2-n-hexyl-1-dodecene
2-n-heptyl-1-undecene
2-n-octyl-1-decene
2-n-nonyl-1-nonene, or any mixtures of the above olefins and etc.

In forming the adduct the vinylidene olefin and the mercaptoethanol are brought together and, while stirring, are maintained at a temperature of about 0° to about 150° C., or even higher, preferably about 26° to about 100° C., and a pressure of about 14.7 to about 300 pounds per square inch gauge (about 1.0 to about 21 kilograms per square centimeter), preferably about 14.7 to about 75 pounds per square inch gauge (about 1.0 to about 5.3 kilograms per square centimeter), for about one minute to about 48 hours, preferably about 10 minutes to about six hours.

Solvents are not needed for adduct formation, although solvents, such as methanol, ethanol, benzene, carbon tetrachloride, chloroform, carbon disulfide, etc., can be used, if desired, for example, to help solubilization when solid olefin feeds are used. Initiators are not needed, although, if desired, such well-known initiators as azobisisobutyronitrile, hydrogen peroxide, tert-butyl hydroperoxide, dibutyl peroxide, cumene hydroperoxide, ultraviolet light, ozone, etc., can be used.

For adduct formation equal molar amounts of reactant olefin and mercaptoethanol are theoretically required. In practice, excess amounts of one of the reactants are used. With a lower vinylidene olefin reactant, for example $C_{10}$ olefin, excess olefin is used, since the excess olefin can readily be removed from the adduct product by flash evaporation. With higher olefins, excess mercaptoethanol is generally used, because the excess mercaptoethanol can be removed easily from the adduct formed merely by washing the same with water.

The adduct so obtained is then reacted with ethylene oxide. This can be done, for example, by adding ethylene oxide to a stirred mixture of adduct containing from about 0.05 to about 5.0 grams, preferably about 0.1 to about 0.5 grams per gram of adduct, of a catalyst, such as sodium or potassium hydroxide or sodium or potassium metal, while maintaining the reaction mixture within a temperature range of about 120° to about 200° C., preferably about 120° to about 150° C., and a pressure of about 14.7 to about 150 pounds per square inch gauge (about 1.0 to about 10.5 kilograms per square centimeter), preferably about 14.7 to about 50 pounds per square inch gauge (about 1.0 to about 3.5 kilograms per square centimeter) for about five minutes to about 10 hours, preferably about 10 minutes to about two hours. The beta,beta-dialkylethylmercaptoethoxylate product obtained will be a mixture of individual beta,-beta-dialkylethylmercaptoethoxylates wherein the average number of ethoxylate units introduced into the adduct will depend on the amount of ethylene oxide used and the reaction conditions employed. In general, at least about three mols of ethylene oxide, preferably about eight to about 26 mols of ethylene oxide, most preferably about eight to about 16 mols of ethylene oxide, will be sufficient to obtain a product containing ethoxylate groups sufficient to satisfy the requirements of the structural formula of the new beta,beta-dialkylethylmercaptoethoxylate claimed herein, as well as to give a substantially completely water-miscible product.

DESCRIPTION OF PREFERRED EMBODIMENTS

The invention defined herein can further be illustrated by the following:

EXAMPLE I

A stirred mixture of 42 grams of Jefferson $C_{12}$ dimer olefin and 21 grams of 2-mercaptoethanol were reacted at a temperature of 26° C. over a period of 48 hours. The reaction product obtained amounted to 57 grams, or a 92 weight percent yield of the adduct

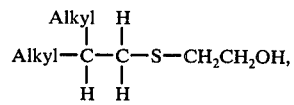

wherein each alkyl group was larger than methyl, with the total number of carbon atoms in the two alkyl groups being 10. The adduct had a refractive index $n_D^{28}$ of 1.4710.

EXAMPLE II

Repeating Example I with 200 grams of Jefferson $C_{14}$ dimer olefin and 105 grams of 2-mercaptoethanol resulted in the production of 263 grams of product, or a 94 weight percent yield of the adduct

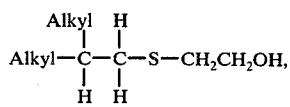

wherein each alkyl group was larger than methyl, with the total number of carbon atoms in the two alkyl groups being 12. The adduct had a refractive index $n_D^{28}$ of 1.4710.

EXAMPLE III

In this run, Example I was repeated using 50 grams of Jefferson $C_{16}$ dimer olefin and 19 grams of 2-mercaptoethanol. There was obtained 61 grams of product or a 91 weight percent yield of the adduct

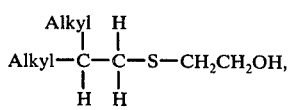

wherein each alkyl group was larger than methyl, with the total number of carbon atoms in the two alkyl groups being 14. The adduct had a refractive index $n_D^{28}$ of 1.4629.

EXAMPLE IV

When the run of Example I was repeated using 52 grams of Jefferson $C_{18}$ dimer and 18 grams of 2-mercaptoethanol, there was obtained 63 grams of product, or a 92 weight percent yield of the adduct

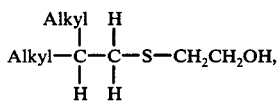

wherein each alkyl group was larger than methyl, with the total number of carbon atoms in the two alkyl groups being 16. The adduct had a refractive index $n_D^{28}$ of 1.4670.

Each of the dimer olefins used in Examples I, II, III and IV are vinylidene olefins manufactured and sold by the Jefferson Chemical Company having the following structural formula:

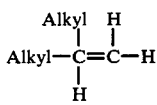

Analysis of each of the above dimer olefins by NMR showed each alkyl in each dimer olefin to be an alkyl group larger than methyl, with the total number of carbon atoms in the combined alkyl groups in each of the dimer olefins used in Examples I, II, III and IV being 10, 12, 14 and 16, respectively.

EXAMPLE V

A mercaptoethanol adduct of a $C_{12}$ internal olefin was prepared as follows. A mixture containing 112 grams of octene-1 and 84 grams of hexene-1 was passed over a catalyst as in Example 5 of U.S. Pat. No. 3,595,920 and the middle fraction corresponding to $C_{12}$ internal olefins was isolated by distillation, b.p. 43°–46° C. at about 0.5 mm Hg. 50 grams of $C_{12}$ internal olefins and 25 grams of 2-mercaptoethanol were reacted, while stirring, at 100° C. for 6 hours. The product was thoroughly washed with water, dried over magnesium sulfate and eluted over silica gel with petroleum ether to separate unreacted olefin. The product was then eluted off the column with ethyl ether which, on evaporation, gave 9.8 grams of an adduct having a refractive index $n_D^{24.5}$ of 1.4770 characterized by the following structure.

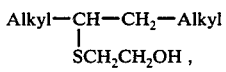

wherein each alkyl group has about the same number of carbon atoms, with the sum of the two alkyl groups being 10.

EXAMPLE VI

A mercaptoethanol adduct of a $C_{14}$ internal olefin was prepared as follows. A batch of $C_{14}$ internal olefin, prepared according to the procedure of Run No. 5 of U.S. Pat. No. 3,595,920 octene-1 as the feedstock, was distilled to obtain a fraction having a boiling point of 70° to 72° C. at 0.3 millimeter of mercury. 80.7 grams of the olefin fraction and 49.8 grams of 2-mercaptoethanol were placed in a 500-milliliter, round-bottomed flask and allowed to react at room temperature with vigorous stirring. After 10 hours there was no evidence of any reaction. Reaction was continued for an additional 4 hours, with the mixture being exposed to a sun lamp, but again no reaction occurred. Finally, the reaction mixture was heated to 115° C. and held at this temperature for two hours, resulting in a clear, homogeneous solution. The product was cooled to room temperature and thoroughly washed several times with water to separate unreacted mercaptoethanol from the product. Unreacted olefin was separated from the adduct by eluting with n-hexane over a silica gel column. The product was isolated by eluting with ethyl ether, followed by evaporation to dryness. The product appeared as a colorless liquid characterized by the following structure:

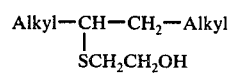

wherein each alkyl group has about the same number of carbon atoms, with the sum of the two alkyl groups being 12, with the refractive index $n_D^{25}$ being 1.4730.

EXAMPLE VII

When Example VI was repeated using decene-1 in place of octene-1 the adduct obtained was a colorless liquid characterized by the following structure:

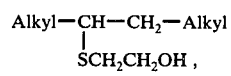

wherein each alkyl group has about the same number of carbon atoms, with the sum of the two alkyl groups being 16, with the refractive index $n_D^{24.5}$ being 1.4783.

A series of runs was made wherein the adduct prepared in each of Examples I to VII above was ethoxylated with ethylene oxide. This was done by placing the adduct in a flask, the flask was then purged with nitrogen and 0.2 gram of sodium metal was added thereto. With the nitrogen purge on, the reaction mixture was heated while maintaining atmospheric pressure, and, while being stirred, ethylene oxide was added thereto through a sparger. Addition of ethylene oxide was continued for about 5.5 hours or until the desired amount of ethylene oxide had been added, after which the mixture was cooled to room temperature and the caustic therein neutralized with phosphoric acid until the final solution was neutral toward litmus paper. While the minimum and the maximum amount of ethylene oxide required to give a completely water miscible product were not determined for each vinylidene olefin reacted, the total ethylene oxide content of around 65 weight percent was sufficient for $C_{12-18}$ olefin derived products to have good solubility properties in water. The resulting product was a mixture of dialkylethylmercaptoethoxylates made up of individual dialkylethylmercaptoethoxylates wherein at least three ethylene oxide unit and in most cases a much larger number of ethylene oxide units had been introduced into the adduct charge molecule. The dialkylethylmercaptoethoxylates obtained were analyzed to determine the average number of ethylene oxide units in the dialkylethylmercaptoethoxylate product and the average molecular weight thereof. The results of these runs are summarized in Table I below.

TABLE I

| Example | Source of Adduct | Starting Olefin | Grams of Adduct | Ethylene Oxide, Grams | Ethoxylation Temperature, °C. | Total Ethylene Oxide Content of Ethoxylated Product, Weight per Cent | Product R—S—(CH₂CH₂O)ₙH | |
|---|---|---|---|---|---|---|---|---|
| | | | | | | | Average Molecular Weight | n, Average |
| VIII | Example I | C₁₂ Jefferson Dimer Olefin | 50.0 | 69.0 | 140-150 | 65.4 | 629 | 8.7 |
| IX | Example II | C₁₄ Jefferson Dimer Olefin | 60.3 | 76.3 | 140-150 | 63.0 | 701 | 9.7 |
| X | Example III | C₁₆ Jefferson Dimer Olefin | 54.0 | 68.0 | 140-150 | 62.0 | 724 | 9.6 |
| XI | Example IV | C₁₈ Jefferson Dimer Olefin | 55.0 | 76.1 | 140-150 | 63.7 | 827 | 11.3 |
| XII | Example V | C₁₂ Internal Olefin | 7.7 | 10.6 | 140-150 | 65.5 | 630 | 8.7 |
| XIII | Example VI | C₁₄ Internal Olefin | 21.2 | 26.7 | 140-150 | 62.8 | 700 | 9.7 |
| XIV | Example VII | C₁₈ Internal Olefin | 5.4 | 7.5 | 140-150 | 63.7 | 828 | 11.3 |

The alkyl substituents in the ethoxylates obtained in each of VIII, IX, X, XI, XII, XIII and XIV correspond to the alkyl substituents in the adducts of Examples I, II, III, IV, V, VI and VII, respectively. By "total ethylene oxide content" of ethoxylated product we mean to include the total CH₂CH₂O— units in the final product. The total ethylene oxide content can be calculated from the following expression:

$$\text{Total Ethylene Oxide Content} = \frac{\text{Weight In Grams of Ethylene Oxide Added} + \text{Weight In Grams Of Adduct} \cdot \frac{44}{\text{Molecular Weight of Adduct}}}{\text{Weight In Grams Of Ethylene Oxide Added} + \text{Weight In Grams Of Adduct}} \times 100$$

Each of the above surfactants was tested for its detergency properties on polyester fabrics using the conventional procedure described by W. G. Spangler et al, *J. Amer. Oil Chem. Soc.*, 42 (8) 724 (1965), with the reflectance being read on a Photovolt Corporation, Model 610, reflection meter. A standard polyester cloth was used for washing, obtained from Testfabrics, Inc., Middlesex, New Jersey. The results obtained are tabulated below in Table II.

TABLE II

| Active Ingredient[1] (Thioglycol Ethoxylate Derived From) | | Prewash | | Postwash | |
|---|---|---|---|---|---|
| | | Soiled | Redeposition | Soiled | Redeposition |
| C₁₂ Internal Olefin | (Example XII) | 17.15 | 87.55 | 28.3 | 63.6 |
| C₁₂ Vinylidene Olefin | (Example VIII) | 17.10 | 88.05 | 31.50 | 84.65 |
| C₁₄ Internal Olefin | (Example XIII) | 18.80 | 90.40 | 18.50 | 71.20 |
| C₁₄ Vinylidene Olefin | (Example IX) | 18.80 | 90.40 | 31.80 | 87.20 |
| C₁₆ Vinylidene Olefin | (Example X) | 18.80 | 90.40 | 28.80 | 91.50 |
| C₁₈ Internal Olefin | (Example XIV) | 17.10 | 87.70 | 18.30 | 73.40 |
| C₁₈ Vinylidene Olefin | (Example XI) | 17.25 | 87.45 | 24.70 | 84.60 |

[1]Detergent formulation: 15 weight per cent nonionic ethoxylate, 35 weight per cent sodium tripolyphosphate, 8 weight per cent sodium silicate and 42 weight per cent sodium sulfate.

The above data in Table II clearly indicate the uniqueness of the beta,beta-dialkylethylmercaptoethoxylates claimed herein. Note the unexpected superiority of the beta,beta-dialkylethylmercaptoethoxylates over the corresponding alpha,beta-dialkylethylmercaptoethoxylates of the same number of carbon atoms as a surfactant for polyester fabrics. In each case wherein the ethoxylate used was derived from a C₁₂, C₁₄ or C₁₈ vinylidene olefin, better detergency was observed and less redeposition occurred than with an ethoxylate derived from the corresponding internal C₁₂, C₁₄ or C₁₈ internal olefins. Although comparable detergency was obtained with an ethoxylate derived from a C₁₂ internal olefin and the one derived from a C₁₆ vinylidene olefin, redeposition was far greater with the C₁₂ internal olefin-derived ethoxylate than with the corresponding C₁₆ vinylidene-derived ethoxylate. Since polyesters in general are particularly difficult to cleanse, this property becomes an especially desirable one in a surfactant.

The superior detergency properties of the vinylidene olefin-derived surfactant over that derived from alpha olefins of comparable carbon number have been clearly demonstrated in our Application Ser. No. 600,150.

Obviously, many modifications and variations of the invention, as hereinabove set forth, can be made without departing from the spirit and scope thereof, and therefore only such limitations should be imposed as are indicated in the appended claims.

We claim:

1. Novel beta,beta-dialkylethylmercaptoethoxylates selected from the group of dialkylethylmercaptoethoxylates of the following structural formulas:

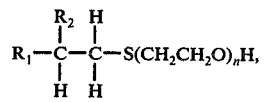

wherein $R_1$ and $R_2$, the same or different, are alkyl substituents having from one to ten carbon atoms, with the number of carbon atoms in $R_1 + R_2$ totaling 10, 14 or 16, and

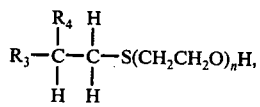

wherein $R_3$ and $R_4$, the same or different, are alkyl substituents having from two to ten carbon atoms, with the total number of carbon atoms in $R_3 + R_4$ totaling 12, and $n$ is an integer greater than 3.

2. Novel beta,beta-dialkylethylmercaptoethoxylates of the following structural formula:

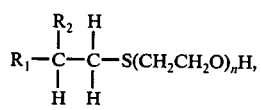

wherein $R_1$ and $R_2$, the same or different, are alkyl substituents having from one to ten carbon atoms, with the number of carbon atoms in $R_1 + R_2$ totaling 10, 14 or 16 and $n$ is an integer greater than 3.

3. Novel beta,beta-dialkylethylmercaptoethoxylates of the following structural formula:

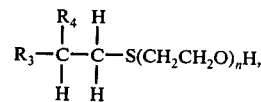

wherein $R_3$ and $R_4$, the same or different, are alkyl substituents, having from two to ten carbon atoms, with the total number of carbon atoms in $R_3 + R_4$ totaling 12 and $n$ is an integer greater than 3.

4. The compounds of claim 2 wherein the total number of carbon atoms in $R_1 + R_2$ is 10.

5. The compounds of claim 2 wherein the total number of carbon atoms in $R_1 + R_2$ is 14.

6. The compounds of claim 2 wherein the total number of carbon atoms in $R_1 + R_2$ is 16.

7. The compounds of claim 2 wherein $n$ is an integer from 8 to 26.

8. The compounds of claim 2 wherein $n$ is an integer from 8 to 16.

9. The compounds of claim 3 wherein $n$ is an integer from 8 to 26.

10. The compounds of claim 3 wherein $n$ is an integer from 8 to 16.

11. The compounds of claim 4 wherein $n$ is an integer from 8 to 16.

12. The compounds of claim 5 wherein $n$ is an integer from 8 to 16.

13. The compounds of claim 6 wherein $n$ is an integer from 8 to 16.

* * * * *